(12) United States Patent
Villalva et al.

(10) Patent No.: US 11,537,589 B2
(45) Date of Patent: *Dec. 27, 2022

(54) METHODS AND APPARATUS FOR EVENT MANAGEMENT

(71) Applicant: MYFITNESSPAL, INC., San Francisco, CA (US)

(72) Inventors: Nicholas Villalva, Austin, TX (US);
Bradford J. Fults, Austin, TX (US);
Andrew Harrison, Austin, TX (US);
Ben Hamill, Austin, TX (US); Carlos Rivera, Austin, TX (US)

(73) Assignee: MYFITNESSPAL, INC., San Francisco, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/815,695

(22) Filed: Mar. 11, 2020

(65) Prior Publication Data

US 2020/0210400 A1    Jul. 2, 2020

Related U.S. Application Data

(63) Continuation of application No. 15/094,395, filed on Apr. 8, 2016, now Pat. No. 10,606,819.

(51) Int. Cl.
*G06F 16/95* (2019.01)
*G06F 16/23* (2019.01)
(Continued)

(52) U.S. Cl.
CPC ...... *G06F 16/2322* (2019.01); *G06F 16/9535* (2019.01); *G16H 20/30* (2018.01); *G16H 40/67* (2018.01)

(58) Field of Classification Search
CPC .... G06F 16/9535; G06F 1/163; G06F 16/335; G06F 16/337; G06F 16/2322; G16H 20/30; G16H 40/67
See application file for complete search history.

(56) References Cited

U.S. PATENT DOCUMENTS

| | | | |
|---|---|---|---|
| 2007/0122780 A1* | 5/2007 | Moon | G09B 19/00 434/236 |
| 2012/0041767 A1* | 2/2012 | Hoffman | A63B 24/0062 705/1.1 |

(Continued)

*Primary Examiner* — Cindy Nguyen
(74) *Attorney, Agent, or Firm* — Maginot, Moore & Beck LLP

(57) ABSTRACT

Apparatus and methods are provided for enabling a sensor device to receive and transmit updates effectively via one or more rules applied to a plurality of event records for transmission by an event management server. In one exemplary embodiment, the event management server manages the plurality of event records (such as records of deletions or updates to a user's profile or goals), via an event suppression application. The event suppression application ensures that event records are not redundantly provided to the sensor device and/or irrelevant records (such as those which no longer contain the most up-to-date information) are not provided to the sensor device. Hence, only the most relevant event records are provided and that those which are not relevant are ignored (not transmitted). In this manner, the sensor device may operate more efficiently to receive only the most relevant transmissions.

22 Claims, 5 Drawing Sheets

(51) Int. Cl.
*G06F 16/9535* (2019.01)
*G16H 20/30* (2018.01)
*G16H 40/67* (2018.01)

(56) References Cited

U.S. PATENT DOCUMENTS

2015/0039757 A1* 2/2015 Petersen ................ H04L 41/16
 709/224
2015/0046933 A1 2/2015 Neilan
2016/0051168 A1* 2/2016 Kamali ................ A61B 5/1123
 600/595
2017/0031449 A1 2/2017 Karsten

* cited by examiner

METHODS AND APPARATUS FOR EVENT MANAGEMENT

CROSS-REFERENCE TO RELATED APPLICATIONS

This application is a continuation of U.S. patent application Ser. No. 15/094,395, filed Apr. 8, 2016, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The present disclosure relates to the field of event management. More particularly, the present disclosure relates to methods, devices, systems, and computer programs for enabling a sensor device to receive and transmit updates effectively via one or more rules applied to a plurality of event records for transmission by an event management server.

BACKGROUND

The background description provided herein is for the purpose of generally presenting the context of the disclosure. Unless otherwise indicated herein, the materials described in this or any section of the disclosure are not prior art to the claims in this application and are not admitted to be prior art by inclusion herein.

Recent advancements in electronics technology has led to the widespread use of portable devices which are able to run computer applications thereon. Accordingly, a wide variety of applications have been developed for mobile use. Among this array of recently developed mobile applications, a large number have been developed which are intended to assist a user in monitoring health-related parameters. These applications utilize data collected by biometric monitoring devices external to the mobile device on which the application is run. Such biometric monitoring applications may include, for example, so-called "smart scales" as well as other wearable devices, such as heart rate monitors and/or activity trackers.

Health-related monitoring applications running on the client devices may utilize data collected at the biometric monitoring devices to monitor activity (e.g., a number of steps taken, flights of stairs, hours of sleep, etc.), measure biometric parameters (e.g., heart rate, blood pressure, etc.), monitor food intake, and/or which measure other environmental parameters (e.g., temperature, altitude, etc.). All of the foregoing may be taken into account within a display that demonstrates a user's progress toward a goal, for example.

In certain instances, it is advantageous to outfit the biometric monitoring device with lower power requirements, low memory, and relatively slow processing capabilities. Such is the case, for example, with certain wearable activity trackers/heart rate monitors, smart scales, etc. This decrease in the overall capabilities of the devices causes a significant problem in providing updates to a user's profile and/or goals on a periodic basis. That is, when changes made by the user at a website or mobile application are to be provided to the sensor device, the sensor device is incapable of receiving and/or processing these updates effectively.

Hence, what is needed is a means for managing a number of events to be provided to a "thin" sensor device. Ideally, such methods and apparatus would enable a sensor device to receive and transmit updates effectively through the use of one or more event suppression rules applied at an event management server. Apparatus and methods for accomplishing the foregoing are provided in the present disclosure.

SUMMARY OF THE DISCLOSURE

The present disclosure addresses the foregoing needs by disclosing, inter alia, methods, devices, systems, and computer programs for event management.

Specifically, methods, apparatus, computer applications, and systems are provided to enable a sensor device to receive and transmit updates effectively via one or more rules applied to a plurality of event records for transmission by an event management server.

These and other aspects of the disclosure shall become apparent when considered in light of the disclosure provided herein.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

All Figures© Under Armour, Inc. 2015-2016. All rights reserved.

DETAILED DESCRIPTION

Exemplary Embodiments

Disclosed embodiments include systems, apparatus, methods and storage medium associated with event management in general, and in particular enabling a sensor device to receive and transmit updates effectively via one or more rules applied to a plurality of event records for transmission by an event management server.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Network Architecture

Figure 1:
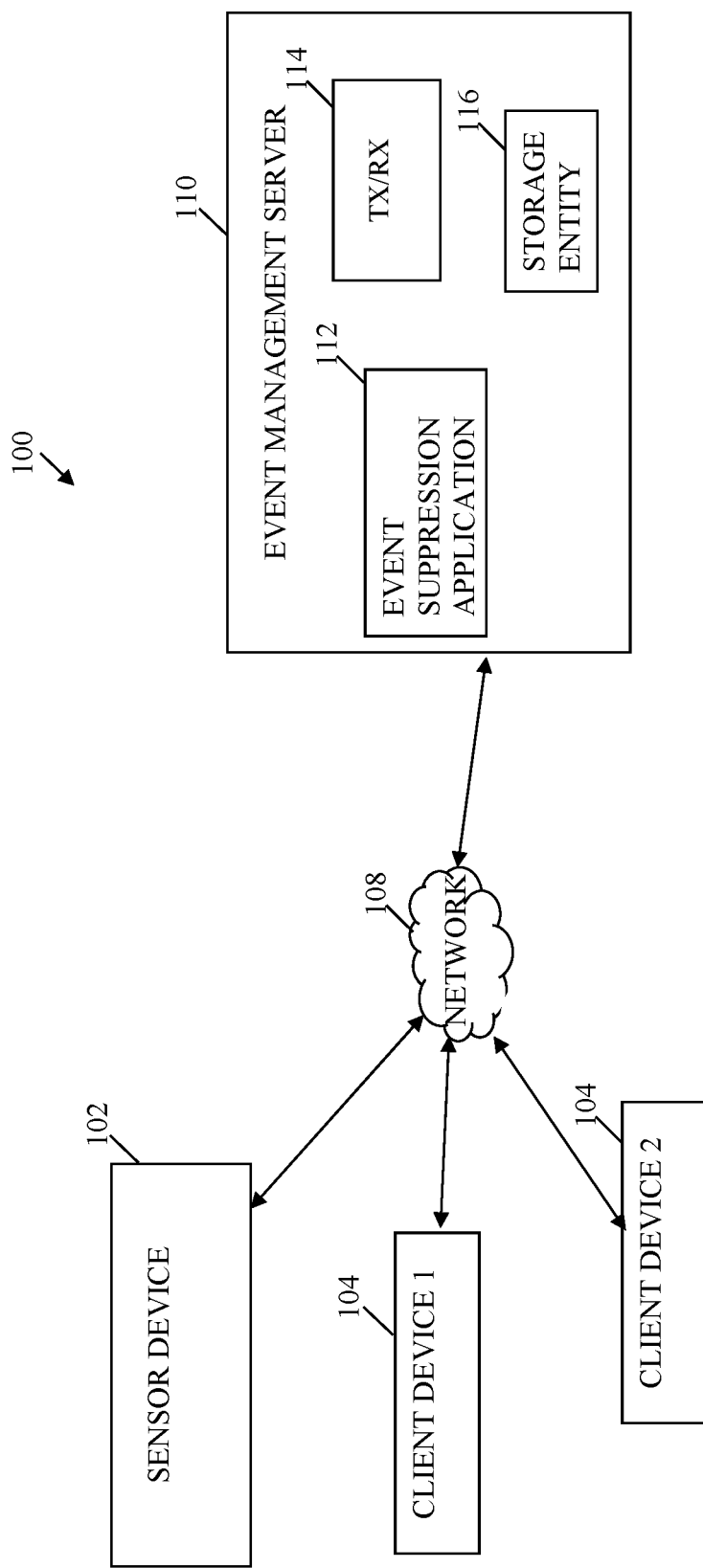
FIG. 1 is a block diagram illustrating an exemplary network for enabling event management including an event management server in accordance with one embodiment of the present disclosure.

Referring now to FIG. 1, an exemplary network 100 for enabling event management in accordance with one embodiment of the present disclosure is illustrated. As shown, the network 100 generally comprises a sensor device 102 in communication with a plurality of client devices 104 and an event management server 110 via a network 108.

The sensor device 102 may comprise one or more portable computing devices designed to measure, sense, monitor, or otherwise receive biometric, environmental, and/or activity parameters. In one variant, certain ones of the sensor devices 102 comprise wearable health-related parameter measurement and computing devices, such as e.g., a smart watch, an activity tracker, a heart rate monitor, a sleep tracking device, a nutrition tracking device, a smart scale, and/or smart eyeglasses. In addition, a sensor device 102 may comprise a smart phone having one or more of the foregoing capabilities and/or which enables user entry of the foregoing parameters. The sensor devices 102 may process data for more than one user profile, as discussed herein.

The sensed data comprises data which the sensor device 102 is configured to collect (such as activity, biometric, and environmental data). For example, an activity tracking device is configured to collect activity data such as steps taken, distance travelled, rate or pace of a run, and/or flights of stairs climbed, etc.; a heart rate monitor is configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. Furthermore, a smart watch and/or smart phone, may be utilized as an activity tracking device, a heart rate monitor, a sleep tracking device, and/or a nutrition tracking device.

The user devices 104 (or client device) comprises a stationary or portable computing apparatus which is configured to run a plurality of software applications thereon (as discussed in detail below) and/or access a web-based application. For example, the user device 101 may comprise a desktop computer (such as those available from Dell Computing of Austin, Tex.), or smartphone, computing tablet, laptop computer, electronic reader, personal digital assistant, and so forth. Exemplary embodiments include e.g., Galaxy S4® from Samsung Electronics of Seoul, Korea, iPhone® or iPad® from Apple Computer of Cupertino, Calif.

In one exemplary embodiment, the user devices 104 run or are configured to access (such as via a web-browser) heath-monitoring applications such as e.g., UA Record™, MapMyFitness®, MyFitnessPal®, Endomondo®, etc. each owned by assignee hereof. Other health activity related monitoring applications may additionally be utilized in connection with the present disclosure, such as those specifically designed to receive information from a particular health monitoring device (i.e., an application which is published by a specific sensor device manufacturer); the foregoing being merely representative of the general concepts of the present disclosure.

In another embodiment, a single user is able to link one or more health-monitoring applications such that he/she is able to sign on once and effect changes in more than one application. Such single sign on abilities are disclosed in co-owned, co-pending U.S. patent application Ser. No. 15/002,036 filed on Jan. 20, 2016 and entitled "Methods and Apparatus for Account Linking", which is incorporated herein by reference in its entirety. As discussed therein, a plurality of applications running on a user device 104 or in communication therewith are able to share data. In one exemplary embodiment, a single user device 104 is configured to run a plurality of heath-monitoring applications which collect data from a respective plurality of sensor devices 102 and/or via user entry; once the applications are linked, the user may make updates or changes to the plurality of applications via entry thereof at a single application. Moreover, once the applications are linked, the user may sign-in to one application and be automatically signed into the other applications.

A user may make changes (including updates and/or deletions) to the user's profile and goals via the client devices 104. These updates are provided to the sensor apparatus 102 to enable the sensor device to display the most accurate information to the user and to utilize the most accurate information to assist the user in his/her progress toward a goal. In addition, the sensor apparatus 102 processes sensed data and provides this information to the client devices 104. The foregoing communications are efficiently made via the event management server 110. Specifically, in one embodiment, the sensor devices 102 are configured to operate with minimized memory, power requirements, and processing capabilities. Hence, it is advantageous to provide a means for transmitting data from the sensor devices 102 and for receiving updates and changes at the sensor device 102 as effectively/efficiently as possible, such as via the event management server 110.

As shown in FIG. 1, the event management entity 110 comprises a server or other computerized apparatus configured to manage a plurality of communication events. The event management server 110 is configured to manage a plurality of event records (such as records of changes to profiles, changes to goals, etc.) via an event suppression application 112. As will be discussed in greater detail below, the event suppression application 112 ensures that event records are not redundantly provided to the sensor device 102 and/or irrelevant records (such as those which no longer contain the most up-to-date information) are not provided to the sensor device 102. That is, in one embodiment, the event suppression application 112 applies one or more rules to a plurality of event records to ensure that only the most relevant event records are provided and that those which are not relevant are ignored (not transmitted).

The exemplary event management server 110, illustrated in FIG. 1, comprises a transceiver apparatus 114. The transceiver 114 enables receipt and transmission of communications to and from the server apparatus 110. For example, the transceiver 114 facilitates the transmission of updates and deletions of profiles and/or goals entered at the client devices 104 to the sensor apparatus 102; the transceiver 114 is also configured to receive sensed/measured/obtained data from the sensor device 102, and updates and deletions of profiles and/or goals entered by a user from a client device 104.

As shown in FIG. 1, the event management server 110 further comprises a storage entity 116 for storage of a plurality of event records (such as records relating to profile updates, profile deletions, goal updates, goal deletions, etc.). The storage entity 116 may further store data sensed, monitored, observed, or otherwise obtained at the sensor devices 102 in one embodiment.

It is appreciated that the event management entity 110 may comprise additional applications which contribute to the functioning thereof as described herein and/or the foregoing functionality may be distributed across more applications or combined into fewer applications. For example, the aforementioned data collection may be provided via a separate application not discussed herein for ease of understanding. The necessary components of the management entity 110 will be clear to a person of ordinary skill in the art given the discussion of the functionality herein.

The network 108 which enables communication between the sensor devices 102, the user devices 104, and the event management entity 110 may comprise a wired and/or wireless, private and/or public network, including e.g., the Internet. Accordingly, each of the monitoring the sensor devices 102, the user devices 104, and the event management entity 110 is configured with appropriate networking communication interfaces (not shown). An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, based stations, and so forth may be placed between the communication interfaces of foregoing devices.

Methodology

Figure 2A:
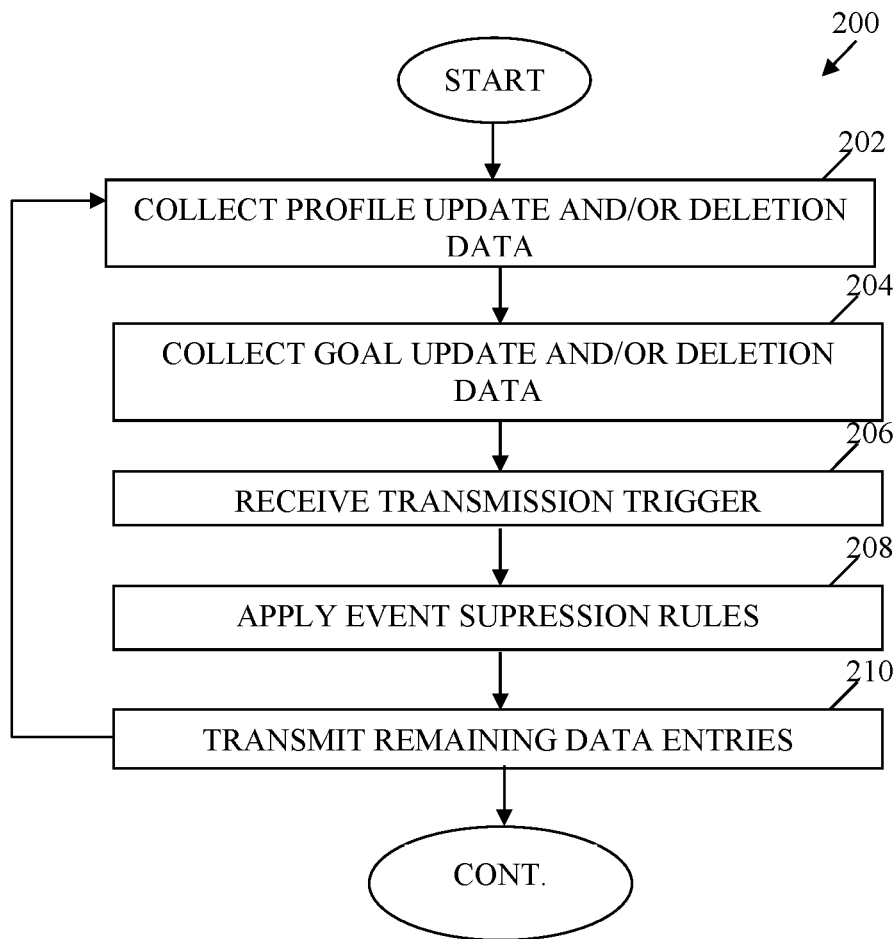
FIG. 2A is a logical flow diagram illustrating an exemplary method for event management in accordance with one embodiment of the present disclosure.

Referring now to FIG. 2, an exemplary method 200 for enabling event management is given. At step 202 of the method, the event management server 110 collects profile update and/or deletion data; per step 204, the event management server 110 further collects goal update and/or deletion data. The data records are collected from the client devices 104 where a user inputs one or more changes or deletions with respect to a profile and/or goal. The generated event records are stored at the storage entity 116 of the event management server 110 in one embodiment. Each record includes a unique identifier which identifies the user profile to which it is associated, e.g., a hashed user identifier, as well as data relating to the removal, update, change, and/or deletion.

In one specific embodiment, the collected data records include the complete profile state or the complete goal state. As noted elsewhere herein, by providing the complete states of the profiles and goals, any prior changes, updates, deletions, etc. are taken into account. That is, a first change to e.g., a user's last name will result in an event record which includes the updated last name, as well as all the other stored data held in the profile record. When the same user logs in later and changes e.g., his first name the complete profile is sent to the server 110 including the updated first name, the updated last name, and all other stored data in the profile record. Accordingly, the most recent event record represents all previous updates, deletions, and data made to that user's goals or profile, and the previous record which reflected the last name change becomes irrelevant.

In one specific embodiment, data records are transported over HTTPS in the body of the request as JSON. The typical representation includes the keys: user_id, event_type, and (optionally) event_data. Exemplary data records are provided in equations 1-4 below.

User Profile Update Record     Eqn. 1
```
{
    "user id": 1234567,
    "event_type": "user_profile_update",
    "event_data": [
        {
            "name": "weight",
            "value": 163.22
        },
        {
            "name": "height",
            "value": 1.332
        },
        {
            "name": "first_name",
            "value": "John"
        },
        {
            "name": "last_name",
            "value": "Smith"
        },
        {
            "name": "nickname",
            "value": "Johnny"
        },
    ]
}
```

User Delete Record     Eqn. 2
```
{
    "user_id": 1234567,
    "event_type": "user_profile_delete"
}
```

User Goal Update Record     Eqn. 3
```
{
    "user_id": 1234567,
    "event_type": "goal_update",
    "event_data": [
        {
            "name": "comparator",
            "value": "lt"
        },
```

```
        {
            "name": "weight_goal",
            "value": 155.0
        }
    ]
}
User Goal Delete Record                             Eqn. 4
{
    "user_id": 1234567,
    "event_type": "goal_delete"
}
```

Next, at step 206, a transmission trigger or notification is received. In one embodiment, the trigger may comprise a user turning on the sensor device 102. In another embodiment, the sensor device 102 is awoke from a "sleep" mode (such as by stepping on a smart scale) and, when this does occur the server 110 is triggered to begin a transmission routine. In yet another embodiment, a user at the sensor device 102 may manually elect to begin update transmissions.

In response to the trigger or notice, the event management server 110 applies one or more event suppression rules at step 208. The event suppression rules, as will be discussed in greater detail below, ensure that redundant and/or irrelevant event records are not transmitted.

Finally, at step 210, the event records which have survived the suppression rules are transmitted to the sensor device 102 and the transmission session is ended. That is, the event records which are not redundant and/or irrelevant are transmitted, whereas suppressed events are ignored or not transmitted. As the appropriate records are ignored or transmitted, each of the evaluated records (i.e., those records whether determined to be irrelevant, redundant, or neither) are flagged as having been viewed or evaluated. In this manner, the server 110 is able to, at a subsequent time, when a new transmission trigger or notification is received, determine at which record it should begin evaluating/applying the suppression rules.

The method 200 continues back to step 202 where additional update and/or deletion data is collected. As noted above, when a subsequent transmission trigger is received (step 206) the event suppression rules are applied to only those events which have not yet been flagged (i.e., which have not yet been evaluated).

Figure 2B:
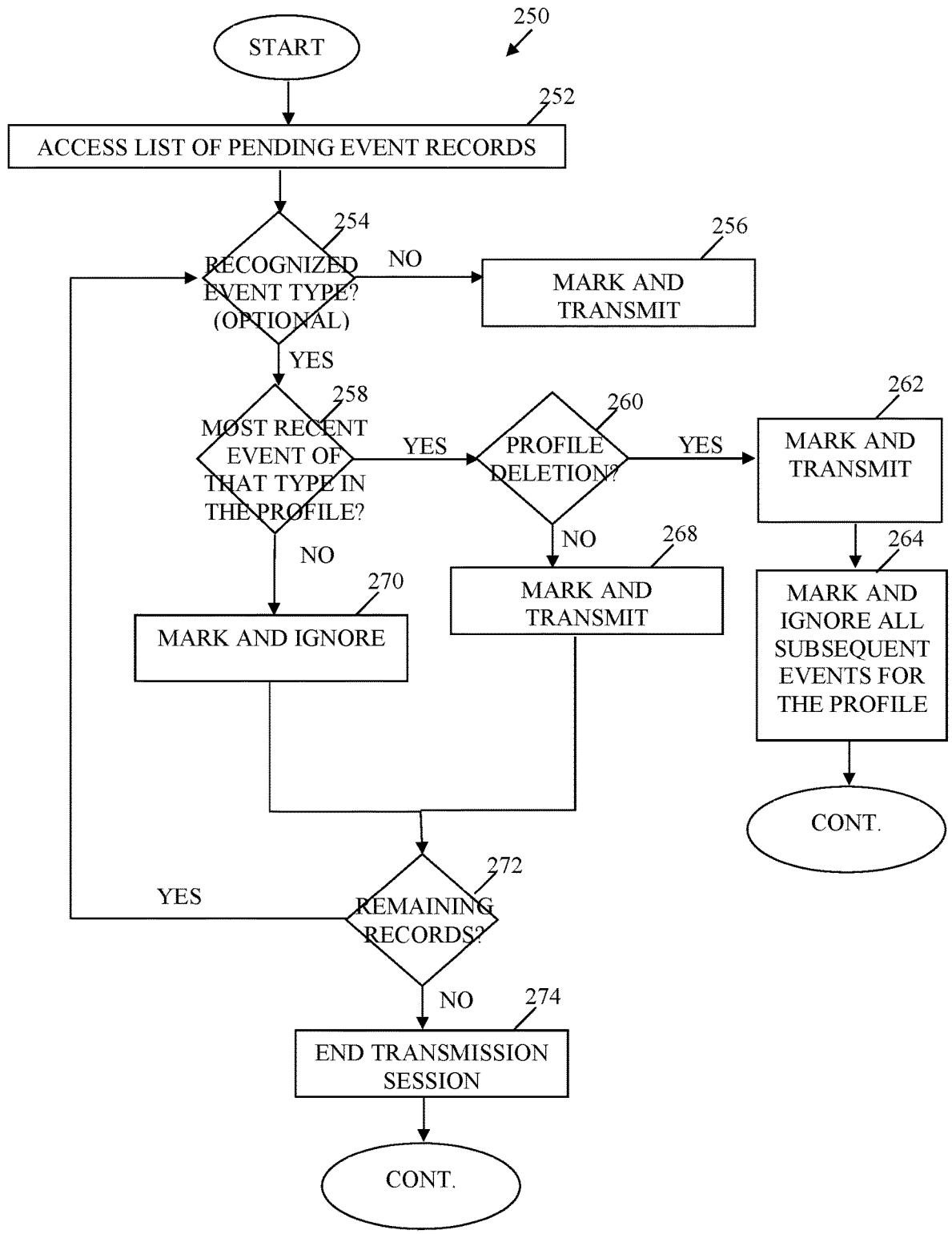
FIG. 2B is a logical flow diagram illustrating a detailed exemplary method for utilizing suppression rules for event management in accordance with another embodiment of the present disclosure.

Referring now to FIG. 2B, a detailed method 250 for event management which outlines an application of one embodiment of the suppression rules is given. As shown, per step 252, a list of pending event records is accessed. The list of events which are pending may be determined based on the presence or absence of a flag indicating review of event records in the storage entity 116. As noted above, in one embodiment, a flag is placed on all records which have been evaluated whether or not these are ultimately transmitted.

Optionally, for each record, it is first determined whether the event type is among those recognized types of event records at step 254. For example, the recognized records may comprise profile records and goal records of the types discussed above. If the record is not among the recognized types, in one embodiment, the record is simply marked as having been evaluated, and then transmitted (step 256). The transmission of an unrecognized event type renders the system upgradable and fully compliant with all event record types. That is to say, event records which are generated at any application are provided to the sensor device 102 for use thereat. This is useful because (i) the event suppression application 112 will only require an update if additional events must be suppressed and (ii) a single, future-compatible location to filter events regardless of event producer/recipient is provided. Without this, any new event type necessitates a change to suppression application 112. Supposing, for example that the number of event types (E) is expected to grow faster than the number of event types requiring suppression (S); the herein disclosed mechanism increases maintainability of the event suppression application 112 by resulting in a simpler application that requires smaller, less-frequent changes.

If the event record is among the recognized event types (e.g., a profile or goal update and/or deletion), at step 258 it is next determined whether the record is the most recent event (in time) of that event type for that profile. That is, the server 110 must determine whether this is e.g., the most recent goal-related record or the most recent profile-related record, etc. for a particular user. As noted above, the most recent record of an event type includes all of the most up-to-date information therein. Hence, all previous updates/changes, etc. are reflected in this most recent record. The newness of an event record may be determined based on e.g., a timestamp on the record; such as a timestamp which is applied by the server 110 when the record is received thereat from the user devices 104. Alternatively, the timestamp may be created at the device which creates the record (e.g., the user device 104) at or near the time the record is generated.

If the event is the most recent, the system will next identify whether the record comprises a profile deletion record at step 260. Profile deletion records are marked as evaluated and transmitted at step 262. Thereafter (step 264), all subsequent events (of any type e.g., profile, goal, etc.) for that profile are marked as evaluated and are ignored (i.e., not transmitted). This ensures that the sensor device 102 will be made aware when a user has deleted his/her profile and will no longer receive and/or store data associated with that user's profile. If the record does not comprise a profile deletion record (determined at step 260), then at step 268 the event is marked as evaluated and transmitted. When it is determined that the record is not the most recent of that event type in the profile (determined at step 258), then at step 270, the event record is marked and ignored (i.e., not transmitted to the sensor device 102).

In either instance (that of step 268 or step 270), the method 250 next determines whether additional records exist which have not yet been evaluated (step 272). This may be determined e.g., by checking for the evaluation flag or marker discussed herein. If records remain, the method 250 begins again at step 254. If no records remain, per step 274, the transmission session is ended. A new session may be begun if and when a subsequent trigger is received.

Figure 2C:
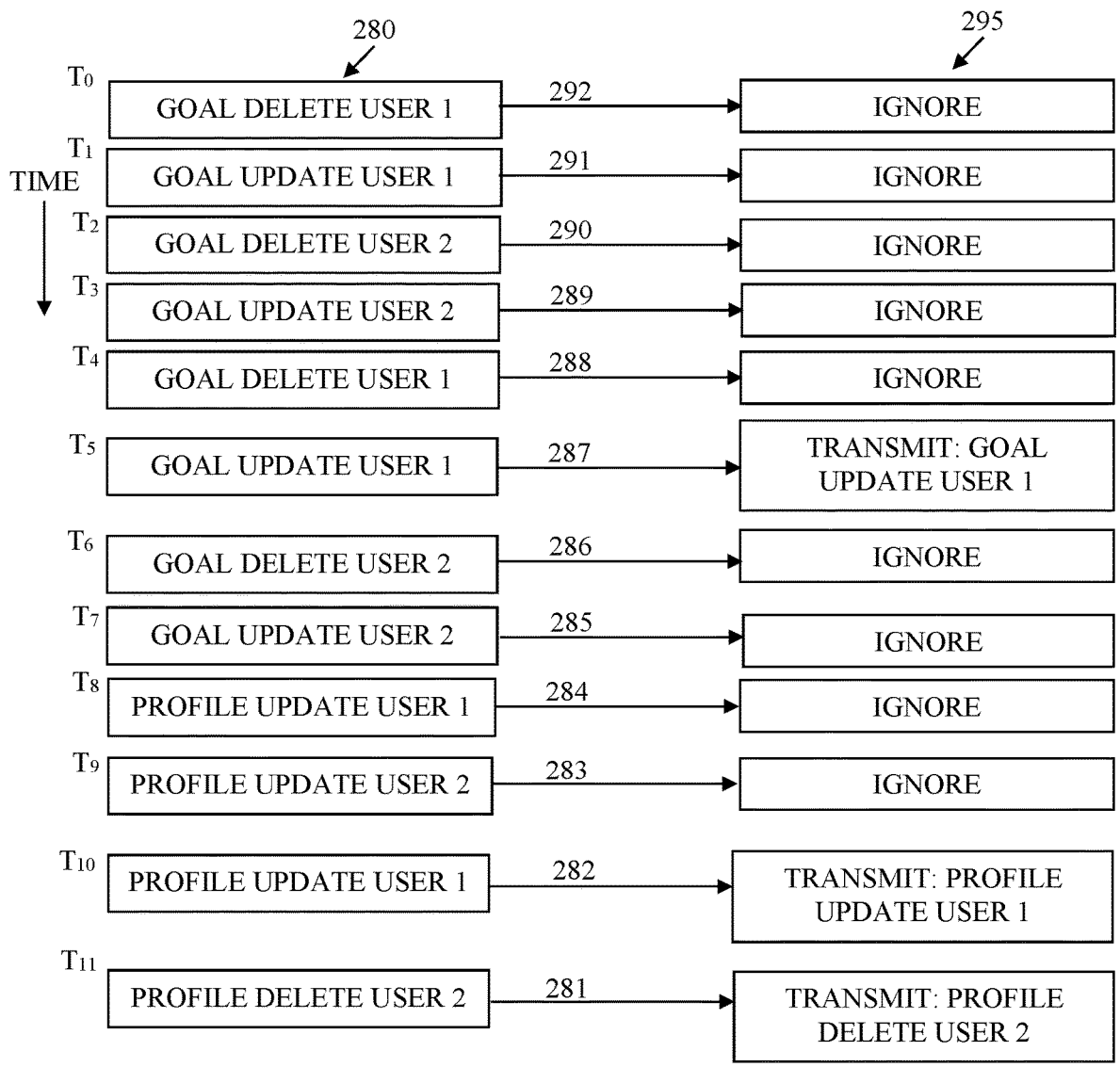
FIG. 2C is a block diagram illustrating an exemplary event record processing using one or more suppression rules in accordance with one embodiment of the present invention.

Referring now to FIG. 2C illustrates an exemplary transmission result 295 after the application of the herein disclosed suppression rules using one specific set of event records 280 is illustrated.

As shown, the records 280 are listed in chronological order from top to bottom, such that the oldest or least recent record in time, $T_0$, is listed at the top of FIG. 2C and the newest or most recent record in time, $T_{11}$, is listed at the bottom of FIG. 2C. Accordingly, the application of suppression rules by the server 110 begins at step 281 with Record $T_{11}$ (i.e., the most recent record).

Record $T_{11}$ comprises a profile deletion record for User 2. Following the rules set forth in FIG. 2B and discussed above, per step 281, it is determined that the record comprises the most recent event of the type (user profile type) in the profile for user 2; therefore, the transmission result 295 is to transmit the record to the sensor 102. Moreover, given the nature of the record as being a profile deletion record, the suppression rules indicate that all subsequent records for that user profile (User 2) regardless of event type should be ignored and not transmitted to the sensor 102.

The next record to be evaluated (step 282), Record $T_{10}$ comprises a profile update for User 1. Again, following the suppression rules discussed herein, Record $T_{10}$ comprises the most recent event of the type (user profile type) in the profile for User 1; therefore, the transmission result 295 is to transmit the record to the sensor 102.

Record $T_9$ comprises a profile update for User 2. As noted above, pursuant to step 283, the application of the suppression rules indicates that this record should be marked as evaluated and not transmitted because User 2 has deleted his/her profile. Similar logic applies at steps 285, 286, 289, and 290 to Records $T_7$, $T_6$, $T_3$, and $T_2$, respectively. Hence, the transmission result 295 for each of these steps comprises marking the records as having been evaluated and then ignoring or not transmitting the records because, as noted above, more recently in time, User 2 has deleted his/her profile.

Record $T_8$ comprises a profile update for User 1. Application of the suppression rules at step 284 includes determining that this is not the most recent event of the type (user profile type) for the user (rather Record $T_{10}$ was the most recent). Therefore, the transmission result 295 is to mark the record as evaluated and ignore it.

Record $T_5$ comprises a goal update for User 1. Application of the suppression rules at step 287, it is determined that Record $T_5$ comprises the most recent event of the type (user goal type) for the user. Therefore, the transmission result 295 is to mark the record as evaluated and transmit it to the sensor 102. It logically follows that any further earlier records for User 1 of the goal type (records $T_4$, $T_1$, and $T_0$) do not comprise the most recent record of the type for the user. Therefore, application of the suppression rules for these records (steps 288, 291, and 292, respectively) results in a transmission result 295 to mark these as evaluated and not transmit these to the sensor 102.

As is evident in the example discussed above, application of the suppression rules renders transmission to the sensor more efficient. Specifically, rather than providing 12 individual update communications (event records), the system now only transmits three.

Figure 3:
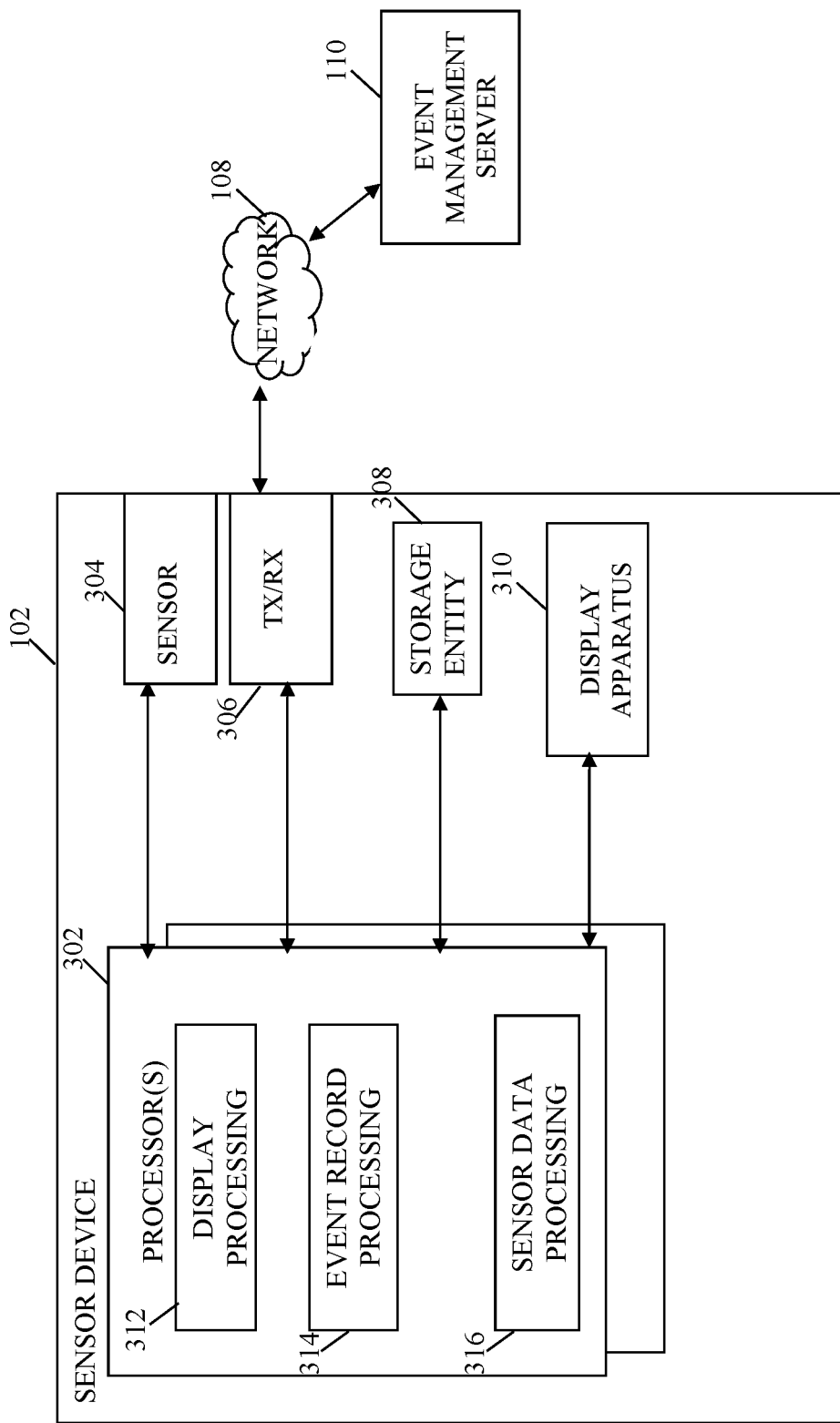
FIG. 3 is a block diagram illustrating an exemplary sensor device configuration in accordance with one embodiment of the present disclosure.

Referring now to FIG. 3, an exemplary sensor device 102 configuration for use with the present disclosure is shown. The sensor device 102, may comprise a computerized apparatus designed to measure, sense, monitor, or otherwise receive biometric, environmental, and/or activity parameters. Exemplary sensor devices 102 may include health-related parameter measurement and computing devices, such as e.g., a smart watch, an activity tracker, a heart rate monitor, a sleep tracking device, a nutrition tracking device, a smart scale, and/or smart eyeglasses. In addition, a sensor device 102 may comprise a smart phone having one or more of the foregoing capabilities and/or which enables user entry of the foregoing parameters. As illustrated above, each sensor device 102 may process data for a number of users (i.e., store multiple profiles).

As illustrated, the device 102 includes one or more processors 302 configured to run one or more software applications thereon (discussed below), a sensor apparatus 304, one or more transceivers 306, a storage apparatus 308, and a display apparatus 310 (optional). Other components of the sensor device 102 may additionally be provided to ensure functioning thereof (not shown). For example, the device 102 may include e.g., input/output devices (such as touchpad, keyboard, cursor control and so forth) and additional communication interfaces (such as network interface cards, modems and so forth), not shown. Moreover, the elements may be coupled to each other via system bus including one or more bridged busses (not shown).

The sensor apparatus 304 comprises an apparatus configured to interact with a user and/or environment in order to sense, observe, measure, or otherwise obtain information about a given parameter (e.g., a health-related parameter). For example, the sensor may collect activity data such as steps taken, distance travelled, rate or pace of a run, and/or flights of stairs climbed, etc.; heartbeat data; data relating to how much time a user/wearer spends sleeping; data relating to food and drinks consumed by a user; data relating to a body weight, body fat percentage, and/or body mass index (BMI), etc.

The transceiver 306 enables communication between the sensor device 102, and the event management entity 110, user devices 104, and other network devices (not shown). Such communication occurs via the network 108. Exemplary communications include, the transceiver 114 receiving updates and deletions of profiles and/or goals entered at the client devices 104 to the sensor apparatus 102; and the interface transceiver 114 transmitting sensed/measured/obtained data from the sensor device 102.

The storage apparatus 308 of the device 102 is utilized to store computer applications to be run by the processor 302 (discussed below). In addition, the storage apparatus is configured to store data relating to each profile associated therewith and the most recent event records for each event record type for each user (and/or information relating thereto) and instructions for various calculations to be performed by the device 102 using the data. The storage apparatus 304 may include mass storage devices such as diskette, hard drive, compact disc read only memory (CD-ROM) and so forth.

A display apparatus 310 is optionally provided on the sensor apparatus 102 in one embodiment. In another embodiment, the display apparatus 310 comprises a separate entity in communication with the sensor apparatus 102. In one variant, the display comprises a user interface (a graphic user interface (GUI)) by which a user may interact with various ones of the applications or programs on the device 102 such as to enter or select a user profile to which sensed or obtained data should be associated, manually enter data, adjust one or more parameters, etc.

The sensor device 102 further includes one or more processors or processor cores 302 configured to run various computer applications thereon, which may be stored at e.g., the storage apparatus 308. For the purpose of this application, including the claims, the terms "processor" and "processor cores" may be considered synonymous, unless the context clearly requires otherwise. The computer applications run by the processor 302 include at least a display processing application 312, an event record processing application 314, and a sensor data processing application 316. These applications are either preloaded on the device 102 at time of manufacture, or downloaded such as via an application server (not shown) in communication with the device 102 via the network 108. Other software applications and processes may be run at the processors 302 to create the herein disclosed features (not shown); the foregoing are merely exemplary. Moreover, the functionality described as attributable to one or more of the foregoing applications may be split across more applications, combined into fewer applications, and/or formed into a single application.

The display processing application 312 comprises a plurality of instructions which are configured to, when executed by the processor 302, process appropriate data in order to generate a display to the user (e.g., a GUI). The display processing application 312 provides, in one embodiment, an identification of the user profile to which sensed or obtained data. In this manner, a user may ensure that data being sensed or obtained is associated to his/her profile. The display processing application 312 may further be configured to display a user's most recent goal settings and/or profile settings. These may be obtained or derived from information identified within the event records transmitted from the event management server 110. Other information, such as alerts, reminders, alarms, etc. may also be provided via the display application 312.

The event record processing application 314 comprises a plurality of instructions which are configured to, when executed by the processor 302, receive and process event records. As discussed elsewhere herein, one or more suppression rules are applied (at a server 110) to a plurality of pending event records prior to delivery thereof to the sensor device 102. Hence, the event record processing application 314 only receives the most recent and relevant records relating to the each user's profile, goals, etc. Processing of these records includes updating the display application 312 and the stored user records with the most recent/relevant information. In addition, the most recent/relevant information derived from the event records is used to calculate certain health-related parameters and/or individual goals. For example, a user's newly entered weight goal received in a goal update event record may be used to calculate a user's daily weight goal by a smart scale in order to ensure progress toward the overall goal in a stated amount of time.

The sensor data processing application 316 comprises a plurality of instructions which are configured to, when executed by the processor 302, receive and process sensed/obtained data. The sensed or obtained data may comprise one or more of: steps taken, distance travelled, rate or pace of a run, and/or flights of stairs climbed, duration of activity, heartbeat data, how much time a user/wearer spends sleeping, food and drinks consumed by a user, body weight, body fat percentage, and/or body mass index (BMI), etc. The sensor data may be placed in a format which may easily be transmitted to the client devices 104, the management server 110 or other sensor data collection entity (not shown).

In one embodiment, the aforementioned processing is performed via coordination of a distributed application having client and network-side components. The network-side component may be run at e.g., the event management entity 110 and the client-side component run at the sensor device 102.

The applications which enable the herein disclosed event management functionality include event suppression application 112, the display processing application 312, the event record processing application 314, and/or the sensor data processing application 316 in the present embodiment. A permanent copy of the programming instructions for these applications (112, 312, 314, and 316) may be placed into permanent storage devices (such as e.g., the storage apparatus 116 and 308) during manufacture of the sensor device 102 and/or event management server 110, or in the field, through e.g., a distribution medium (not shown), such as a compact disc (CD), or from a distribution server (not shown) via the network 108. That is, one or more distribution media having an implementation of the agent program may be employed to distribute the agent and program various computing devices.

The herein described event suppression application 112 improves the functioning of the event management server 110 by enabling it to provide a compact number of non-redundant and relevant event records to a sensor device 102 which enables the sensor device 102 to receive and utilize the event records more efficiently than would be possible had it received a non-compact number of event records (including redundant and/or irrelevant records). Furthermore, devices that are able to manage event records as disclosed herein can operate more efficiently to enable faster processing at a device receiving the event records.

The herein described sensor device 102 applications (312, 314, and 316) improve the functioning of the sensor device 102 by enabling it to efficiently process event records in order to provide a user interface which enables a user/operator to examine the health related parameters sensed or obtained thereby. Furthermore, devices that are able to efficiently process event records can operate more efficiently to assist a user in viewing health-parameter data and establishing and maintaining healthy lifestyle patterns.

In summary, a method of managing a number of event records to be communicated between one or more user device and a second device relating to the user is disclosed. In one embodiment, the method comprises: (i) accessing a list of pending event records at a server entity; (ii) determining whether a first one of the pending event records comprises a most recent event of an event record type associated to a first user profile; (iii) when it is determined that the first one of the pending event records comprises the most recent event of the event record type associated to the first user profile, transmitting the first one of the pending event records to the second device; (iv) when it is determined that the first one of the pending event records does not comprise the most recent event of the event record type associated to the first user profile, omitting to transmit the first one of the pending event records to the second device; and (v) performing the acts of determining and transmitting or omitting for each additional event record listed in the list of pending event records.

In addition, a server apparatus for management of transmission of a plurality of records relating to a respective plurality of events entered at one or more user devices to at least one health-monitoring device is disclosed. In one embodiment, the apparatus comprises: at least one interface configured to enable communication with the at least one health-monitoring device; a storage entity; and a processor configured to communicate to the storage entity, and the at least one interface, the processor configured to execute a plurality of health-monitoring computer programs and at least one event management computer program thereon, the event management computer program comprising a plurality of instructions which are configured to, when executed by the processor, cause the server apparatus to: (i) access a plurality of previously unevaluated event records; (ii) determine whether a first one of the plurality of previously unevaluated event records comprises a most temporally recent event of an event record type associated to a first user profile within the plurality of the previously unevaluated event records; (iii) transmit the first one of the plurality of previously unevaluated event records to the at least one health-monitoring device when it is determined that the first one of the plurality of previously unevaluated event records comprises the most temporally recent event of the event record type associated to the first user profile within the plurality of the previously unevaluated event records; and (iv) not transmit the first one of the plurality of previously unevaluated event records to the at least one health-monitoring device when it is determined that the first one of the plurality of previously unevaluated event records does not comprise the most temporally recent event of the event record type associated to the first user profile.

Furthermore, a non-transitory, computer readable medium is disclosed. In one embodiment, the non-transitory, computer readable medium comprises a plurality of instructions which are configured to, when executed: (i) collect at a server entity a plurality of event records representative of a respective plurality of events entered at one or more user devices and communicated to the server entity via a network; (ii) receive a notification that a second device is able to accept one or more of the plurality of event records; (iii) apply one or more rules configured to identify for suppression first ones of the plurality of event records which are not required to be transmitted to the health monitoring device, and identify for transmission second ones of the plurality of event records which are required to be transmitted to the health monitoring device; (iv) cause the first ones of the plurality of event records to be marked as having been evaluated; (v) cause the second ones of the plurality of event records to be marked as having been evaluated; and (vi) cause the second ones of the plurality of event records to be transmitted to the health monitoring device.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of reducing a number of event records to be communicated between two or more user devices including a device configured to obtain event data corresponding to health-related parameters for a user, said method comprising:
    accessing a list of pending event records at a first user device, said pending event records corresponding to health-related parameters for the user, wherein said pending event records are identified by a flag indicating review of said event record and queued for transmission to said device configured to obtain said event data;
    determining whether a first one of said pending event records comprises a most recent event of an event record type associated to the user;
    when it is determined that said first one of said pending event records comprises said most recent event of said event record type associated to the user, transmitting said first one of said pending event records to said device configured to obtain said event data;
    when it is determined that said first one of said pending event records does not comprise said most recent event of said event record type associated to said user, omitting to transmit said first one of said pending event records to said device configured to obtain said event data such that the number of event records to be communicated is reduced; and
    performing said acts of determining and transmitting or omitting for each additional event record listed in said list of pending event records.

2. The method of claim 1, further comprising determining whether said first one of said pending event records comprises a recognized event type.

3. The method of claim 2, wherein when said first one of said pending event records does not comprise a recognized event type, said method further comprises transmitting said first one of said pending event records to said device configured to obtain said event data.

4. The method of claim 3, wherein when said first one of said pending event records does not comprise a recognized event type, said method further comprises marking said first one of said pending event records as having been evaluated.

5. The method of claim 1, wherein said event records include event records corresponding to one or more changes or updates relating to a user profile or goal.

6. The method of claim 1 further comprising:
    determining whether said first one of said pending event records comprises a record indicating a first user profile deletion; and
    when it is determined that said first one of said pending event records comprises a record indicating said user profile deletion, omitting to transmit other ones of said pending event records to said device configured to obtain said event data.

7. The method of claim 1 wherein, when it is determined that said first one of said pending event records comprises said most recent event of said event record type, or when it is determined that said first one of said pending event records does not comprise said most recent event of said event record type, said method further comprising marking said first one of said pending event records as having been evaluated.

8. The method of claim 1, further comprising ending a transmission session when it is determined that no further event records are listed in said list of pending event records.

9. The method of claim 1 wherein said device configured to obtain event data relating to a user is an activity tracking device and wherein said health-related parameters are activity-related parameters generated by the activity tracking device.

10. The method of claim 9 wherein said event data corresponding to health-related parameters is collected based on user-activation of the activity tracking device.

11. A server apparatus for reducing transmission of a plurality of records relating to a respective plurality of events entered at one or more user devices including at least one activity tracking device, said events corresponding to health-related parameters for the user, said server apparatus comprising:
    at least one interface configured to enable communication with said at least one activity tracking device;
    a storage entity; and
    a processor configured to communicate to said storage entity, and said at least one interface, said processor configured to execute a plurality of health-monitoring computer programs and at least one event management computer program thereon, said event management computer program comprising a plurality of instructions which are configured to, when executed by said processor, cause said server apparatus to:

access a plurality of previously unevaluated event records corresponding to health-related parameters for the user, wherein said previously unevaluated event records are queued for transmission;

determine whether a first one of said plurality of previously unevaluated event records comprises a most temporally recent event of an event record type associated to a first user profile within said plurality of said previously unevaluated event records;

transmit said first one of said plurality of previously unevaluated event records to said at least one health-monitoring device when it is determined that said first one of said plurality of previously unevaluated event records comprises said most temporally recent event of said event record type associated to said first user profile within said plurality of said previously unevaluated event records; and not transmit said first one of said plurality of previously unevaluated event records to said at least one health-monitoring device when it is determined that said first one of said plurality of previously unevaluated event records does not comprise said most temporally recent event of said event record type associated to said first user profile, and thereby reduce a number of the plurality of event records transmitted by the server apparatus.

12. The server apparatus of claim 11, wherein said determination, transmission and non-transmission occur for each of said plurality of previously unevaluated event records.

13. The server apparatus of claim 11, wherein said plurality of instructions are further configured to, when executed by said processor, cause said server apparatus to:
determine whether said first one of said plurality of previously unevaluated event records comprises a recognized event type; and
when said first one of said plurality of previously unevaluated event records does not comprise said recognized event type, transmit said first one of said plurality of previously unevaluated event records to said at least one health-monitoring device.

14. The server apparatus of claim 13, wherein said plurality of instructions are further configured to, when executed by said processor, cause said server apparatus to:
when said first one of said plurality of previously unevaluated event records does not comprise said recognized event type, place a marker on said first one of said plurality of previously unevaluated event records as having been evaluated.

15. The server apparatus of claim 11 wherein said plurality of instructions are further configured to, when executed by said processor, cause said server apparatus to:
place a marker on said first one of said plurality of previously unevaluated event records as having been evaluated; and
determine based on a presence of said marker on each of said plurality of previously unevaluated event records that no further event records are pending, and end a transmission session.

16. The server apparatus of claim 11, wherein said plurality of instructions are further configured to, when executed by said processor, cause said server apparatus to:

when it is determined that said first one of said plurality of previously unevaluated event records comprises a record indicating a profile deletion associated to said first user profile, not transmit any other ones of said plurality of previously unevaluated event records associated to said first profile to said at least one health-monitoring device.

17. A non-transitory, computer readable medium comprising a plurality of instructions which are configured to, when executed:
collect, at a first device of an activity tracking system, a plurality of pending event records representative of a respective plurality of events entered at one or more user devices and communicated to said first device via a network, wherein said pending event records correspond to health-related parameters for a user, and wherein said pending event records are queued for transmission and identified by a flag indicating review of said event record;
receive a notification that a second device of the activity tracking system is able to accept one or more of said plurality of pending event records;
apply one or more rules configured to identify for suppression first ones of said plurality of pending event records which are not required to be transmitted to said second device, and identify for transmission second ones of said plurality of pending event records which are required to be transmitted to said second device;
cause said first ones of said plurality of pending event records to be marked as having been evaluated;
cause said second ones of said plurality of pending event records to be marked as having been evaluated; and
cause said second ones of said plurality of pending event records to be transmitted to said second device without causing said first ones of said plurality of pending event records to be transmitted to said second device such that a number of event records transmitted to said second device is reduced.

18. The non-transitory, computer readable medium of claim 17, wherein said notification that said second device is able to accept said one or more of said plurality of pending event records comprises a notification generated when said second device is powered on.

19. The non-transitory, computer readable medium of claim 17, wherein said first ones of said plurality of pending event records do not include most recent event records of event record types, and said second ones of said plurality of pending event records including most recent event records of the event record types.

20. The non-transitory, computer readable medium of claim 17, wherein one or more rules configured to identify for suppression first ones of said plurality of pending event records which are not required to be transmitted to said second device comprise rules configured to identify redundant and/or irrelevant event records from among said plurality of pending event records.

21. The method of claim 1, wherein the event data corresponding to health-related parameters for a user includes food and drink consumption data.

22. The method of claim 1 wherein at least one of the two or more user devices is a nutrition tracking device.

* * * * *